United States Patent [19]

Groenendaal et al.

[11] Patent Number: 5,264,222
[45] Date of Patent: Nov. 23, 1993

[54] ORAL PHARMACEUTICAL COMPOSITIONS IN UNIT DOSAGE FORM

[75] Inventors: Jan W. Groenendaal, Delft; Aart Muhlenbruch, Haarlem, both of Netherlands

[73] Assignee: Gist-Brocades N.V., Delft, Netherlands

[21] Appl. No.: 908,950

[22] Filed: Jul. 6, 1992

Related U.S. Application Data

[63] Continuation of Ser. No. 560,777, Jul. 31, 1990, abandoned.

[30] Foreign Application Priority Data

Jan. 9, 1990 [EP]  European Pat. Off. ........ 90200064.5

[51] Int. Cl.$^5$ ............................................. A61K 9/48
[52] U.S. Cl. ..................................... 424/451; 424/464
[58] Field of Search ............... 424/451, 489, 458, 452, 424/464

[56] References Cited

U.S. PATENT DOCUMENTS

| | | | |
|---|---|---|---|
| 4,193,985 | 3/1980 | Bechgaard | 424/462 |
| 4,670,245 | 6/1987 | Vasquez et al. | 424/9 |
| 4,689,229 | 8/1987 | Banik | 514/57 |

FOREIGN PATENT DOCUMENTS

| | | |
|---|---|---|
| 0206625 | 12/1986 | European Pat. Off. |
| 282132 | 9/1988 | European Pat. Off. |
| 022834 | 5/1987 | PCT Int'l Appl. |

Primary Examiner—Thurman K. Page
Assistant Examiner—Leon R. Horne
Attorney, Agent, or Firm—Emmanual J. Lobato; Robert E. Burns

[57] ABSTRACT

Oral pharmaceutical compositions in unit dosage form, especially capsules, comprising solid Colloidal Bismuth Subcitrate (CBS), optionally one or more auxilliary medicaments and excipients, the dosage units having a packing density of between 0.06 and 0.60 grams of CBS per ml.

31 Claims, 2 Drawing Sheets

ORAL PHARMACEUTICAL COMPOSITIONS IN UNIT DOSAGE FORM

This is a continuation of application Ser. No. 07/560,777, filed Jul. 31, 1990, now abandoned.

This invention relates to oral pharmaceutical compositions in unit dosage form, comprising solid Colloidal Bismuth Subcitrate.

Solid Colloidal Bismuth Subcitrate (CBS), Trademark De-Nol® of Gist-brocades N.V., is the product of European Patent 0,075,992, corresponding to U.S. Pat. No. 4,801,608, the contents of which are incorporated herein by reference in their entirety. It is also the active ingredient of British Patent 1,478,742. According to these specifications, CBS can be formulated into pharmaceutical compositions in solid dosage form for oral administration, such as tablets and capsules. Up to now only the tablet form has been realized and it is marketed in many countries.

According to The Merck Manual, 11th Edition (1989), item 1296, the approximate molecular formula of CBS is $K_3(NH_4)_2[Bi_6O_3(OH)_5(C_6H_5O_7)_4]$. Its bismuth content, when expressed as $Bi_2O_3$, is according to said EP 0,075,992 and U.S. Pat. No. 1,478,742, 39–42% by weight.

The currently used swallowable tablet form of CBS has already been given to hundreds of thousands of patients and its clinical efficacy and safety are firmly established. However, recently there have been reports of a transient sharp peak of bismuth blood level in humans after the ingestion of this CBS-containing swallowable tablet, $t_{max}$ around 30 minutes, see C. U. Nwokolo et al., Aliment. Pharmacol. Therap. 3, 1989, 29–39. On the other hand, the value of the traditionally cited safety blood levels of bismuth has also been questioned recently, see for Example A. Slikkerveer and F. de Wolff, Med. Toxicol. Adverse Drug Exp. 4 (5) 1989, 303–323. Anyway, since the therapeutic action of CBS is localized in the gastrointestinal tract, even a transient peak of bismuth blood level does not appear to serve any useful purpose and should be avoided if possible.

The object of the present invention therefore is to provide an oral dosage unit comprising CBS in a therapeutically effective amount, which does not cause the above described peak in the bismuth blood levels. This object has now been found to be met by oral pharmaceutical dosage units, comprising CBS prepared according to any of the above identified patent specifications, provided that the packing density of the CBS in the dosage units is between 0.06 and 0.60 g/ml.

The term "packing density" as used herein, means the weight of the active ingredient (CBS) in grams divided by the volume occupied by the dose form expressed in milliliters, and, in case of a filled capsule form, excludes the volume and weight of the capsule container. Thus, the packing density can be varied by varying the amount of excipients added to the CBS and by varying the pressure used in compressing the units.

The invention therefore concerns oral pharmaceutical compositions in unit dosage form comprising a therapeutically effective amount of solid Colloidal Bismuth Subcitrate (CBS), and, optionally, pharmaceutically acceptable excipients, characterized in that the packing density of the CBS in the pharmaceutical dosage units is between 0.06 and 0.60 g/ml.

Preferably, the packing density is 0.30–0.50 g/ml.

FURTHER DETAILS OF THE INVENTION

Figure 1:
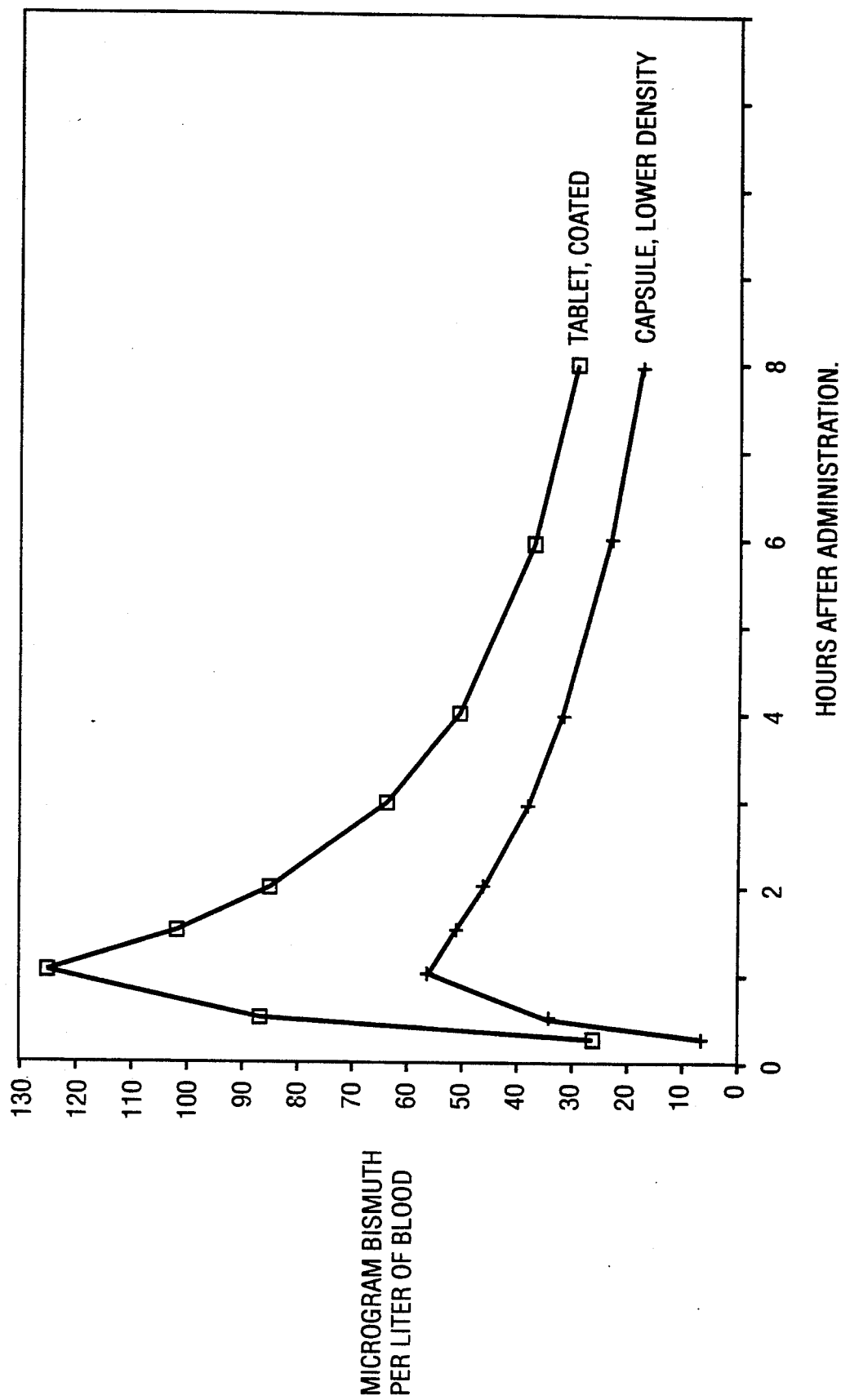
FIG. 1: a graphic representation of mean bismuth blood levels in dogs after ingestion of different CBS formulations.

The CBS according to the invention is preferably in the form of a granulate, having a preferred particle size of less than 1.5 mm.

To the CBS may be added any of the excipients known in the art, which are compatible with CBS, such as:

diluents, like lactose, starch, microcrystalline cellulose, sorbitol, mannitol, dibasic calcium phosphate dihydrate, calcium sulfate dihydrate, sucrose-based diluents and mixtures thereof;

binders, like acacia, cellulose derivatives, gelatin, glucose, polyvinylpyrollidone, starch, sucrose, sorbitol, tragacanth, sodium alginate and mixtures thereof;

disintegrants, like microcrystalline cellulose and cellulose derivatives, starch and its derivatives, alginic acid and its derivatives, ion-exchange resins, cross-linked sodium carboxymethyl cellulose, sodium starch glycolate, cross-linked polyvinylpyrrolidone and formaldehyde-caseine;

lubricants, antiadherents and glidants, like magnesium-, calcium- and sodium stearates, stearic acid, hydrogenated castor oil, talc, water, polyethylene glycol, sodium lauryl sulfate, magnesium lauryl sulfate and silica.

These excipients are preferably added in a total amount ranging from 3–1000 mg, more preferably 20–150 mg, per 100 mg of CBS.

A low packing density of oral dosage units as specified above is contrary to the current tendency in the art of pharmaceutical production, which is to concentrate the oral dosage units, e.g. by compressing the contents of oral capsules to a high density, see Hard Capsules, Development and Technology, Ed. K. Ridgway 1987, chapter 9, G. C. Cole, pp. 92–103.

The oral dosage units of the present invention, when compared to swallowable tablets comprising the same formula and dosage of CBS but with a higher density, were found to give not only a lower maximal blood and plasma bismuth level ($C_{max}$), but also a lower blood and plasma bismuth rise (AUC) and a lower bismuth excretion in the urine. Therefore, systemic bismuth absorption after ingestion of these dosage units has proved to be lower than after ingestion of the tablets. This is contrary to the expectation that more dispersible material leads to its more rapid dissolution and consequently to its greater absorption than compressing the same material.

The oral dosage units of the present invention surprisingly give maximum bismuth plasma levels and a total bismuth absorption which are lower than that of the denser dosage units.

Besides CBS, the oral dosage units according to the invention may also contain auxiliary medicaments, preferably those which are intended to act in combination with it, such as non-steroidal anti-inflammatory compounds, $H_2$-antagonists and synthetic prostaglandins. In particular the dosage units may contain antimicrobially effective medicaments such as antibiotics and chemotherapeutic compounds, more in particular medicaments effective against *Helicobacter pylori* (formerly called *Camoylobacter pylori*), such as the antimicrobially effective nitro imidazoles, the β-lactam antibiotics such as the penicillins, cephalosporins, monobactams and penems, the tetracyclines, the quinolones and the macrolides.

The preferred dosage of CBS in the oral dosage units according to the invention is 30–600 mg per dosage unit, more preferably 37.5–300 mg per dosage unit.

The dosage of the optionally present auxiliary medicaments will depend on the effectivity of the particular medicament used.

The most practical oral dosage units according to the invention are capsules, although tablets having a low CBS density as defined above are also possible.

The material of swallowable capsules according to the invention may be any of those known in the art, such as gelatine, modified starches, such as hydroxyalkyl starch, and cellulose derivatives, such as cellulose ethers, e.g. methyl cellulose. Gelatine capsules can be soft and hard.

The dosage units according to the invention may be further coated in order to provide for controlled release.

The following Examples will illustrate the invention.

EXAMPLE 1

CBS, prepared according to European Patent 0,075,992 and U.S. Pat. No. 4,801,608, was used to prepare tablets and capsules as follows:

Uncoated swallowable tablets containing CBS were produced as follows: 100 kg of CBS was granulated with 23.8 kg of corn starch using 5.85 kg of povidone K30 dissolved in 51.0 kg of ethanol. The granulate, having a particle size of less than 1 mm, was blended with 7.8 kg of polacrilin potassium, 1.98 kg of polyethylene glycol 6000 and 0.66 kg of magnesium stearate, and compressed into tablets.

Coated swallowable tablets containing CBS were produced by filmcoating the above described compressed tablets with about 12 mg hydroxypropyl methylcellulose and about 2 mg polyethylene glycol per tablet. These tablets were identical to commercially used De-Nol ® swallowable tablets.

Swallowable capsules with a lower-density and with a higher-density content were produced using the granulate for uncoated swallowable tablets as described above, filled into hard gelatin capsules No. 0, using a rotary capsule filling machine. The packing density of the capsule content was adjusted by settings of the piston within the dosator.

The densities of the uncoated and coated tablets and of the contents of the two different capsules were calculated with respect to the amount of CBS per units of volume.

The results are presented in the following Table 1:

TABLE 1

|  | Packing volume of one dosage form | Packing density (amount of CBS) |
|---|---|---|
| Tablet, uncoated | 0.25 ml | 1200 mg/ml |
| Tablet, coated | 0.25 ml | 1200 mg/ml |
| Content capsule, lower density | 0.70 ml | 429 mg/ml |
| Content capsule, higher density | 0.50 ml | 600 mg/ml |

EXAMPLE 2

Bismuth absorption in dogs

Healthy fasted dogs (Beagles) were given a single dose of coated tablets or the lower-density capsules of Example 1. The dogs were each dosed with 2 tablets or 2 capsules, giving a total dose of 600 mg CBS per dog. After ingestion, blood samples were taken at 9 intervals up to 8 hours.

The bismuth content was measured in the blood by atomic absorption.

The mean bismuth blood levels in the dogs after ingestion of the different CBS formulations are given in FIG. 1.

Table 2 summarizes the means of:

the blood $t_{max}$ (time after ingestion at which maximum bismuth blood level was reached);

the blood $C_{max}$ (maximum bismuth blood level reached);

the blood AUC (Area Under bismuth concentration-time Curve), calculated over a period of 8 hours after dosage.

TABLE 2

| Formulation | Number of dogs | Mean parameters calculated from the bismuth blood concentration data | | |
|---|---|---|---|---|
| | | $t_{max}$ (hours) | $C_{max}$ (μg/L) | AUC (μg · L$^{-1}$ · h) |
| Coated tablet | 8 | 1.06 | 132.0 | 462 |
| Lower-density capsule | 12 | 1.13 | 60.6 | 252 |

From these results it is clear that in dogs the lower-density capsules gave a lower systemic bismuth absorption than did a prior art dosage form.

EXAMPLE 3

Bismuth absorption in humans

Healthy fasted human volunteers were dosed with the uncoated and coated tablets and the two different capsules of Example 1. The volunteers were each dosed with 2 tablets or 2 capsules, giving a total dose of 600 mg CBS per volunteer. After ingestion blood samples were taken at several intervals up to 3 hours, and the urine was collected for 3 hours.

The bismuth content was measured in the plasma and in the urine by atomic absorption.

Figure 2:
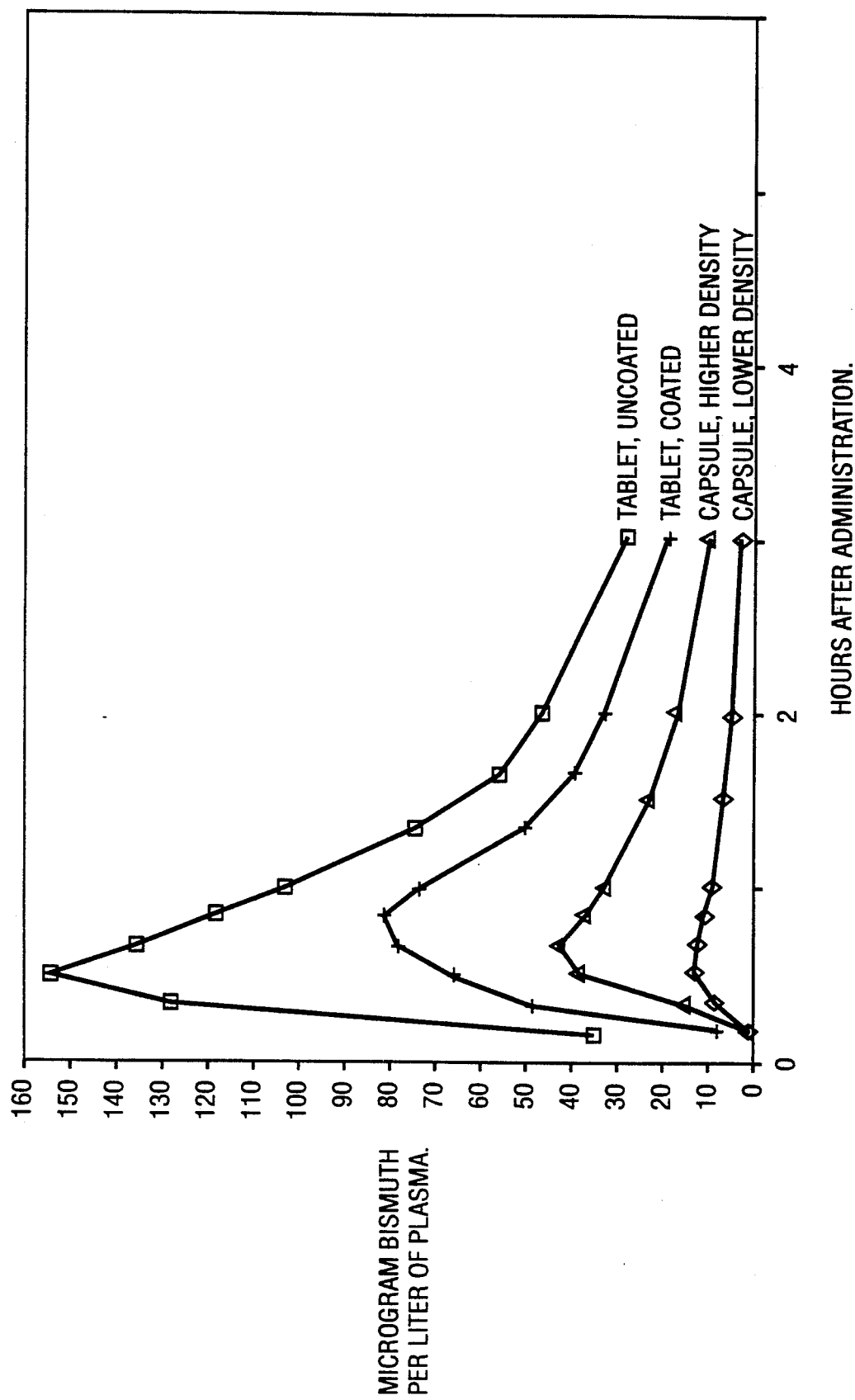
FIG. 2: a graphic representation of mean bismuth plasma levels in humans after ingestion of different CBS formulations.

The mean bismuth plasma levels in humans after ingestion of the different CBS formulations are given in FIG. 2.

Table 3 summarizes the plasma and urine data under the same headings as Table 2 (AUC calculated over a period of 3 hours after dosage, urine collected over a period of 3 hours after dosage).

TABLE 3

| Formulation | Number of volunteers | Mean parameters from the bismuth plasma concentration data | | | Bismuth in urine (μg) |
|---|---|---|---|---|---|
| | | $t_{max}$ (hrs) | $C_{max}$ (μg/L) | AUC (μg · L$^{-1}$ · h) | |
| Uncoated tablet | 6 | 0.41 | 161.2 | 211 | 747.8 |
| Coated tablet | 12 | 0.58 | 95.1 | 128 | 394.9 |
| Lower-density capsule | 12 | 0.54 | 14.7 | 20 | 39.3 |
| Higher-density capsule | 12 | 0.60 | 47.8 | 64 | 181.8 |

From the above results it is clear, that also in humans the lower-density capsules gave a much lower systemic bismuth absorption than did the prior art dosage forms, the higher-density capsule being intermediate. From Tables 3 and 1 there appears a reverse relationship between the density of the dosage form and the systemic bismuth absorption therefrom.

We claim:

1. An oral pharmaceutical composition in unit dosage form comprising a safe and effective amount of solid Colloidal Bismuth Subcitrate (CBS) and, optionally, pharmaceutically acceptable excipients, wherein the packing density of the CBS in each unit of the pharmaceutical composition is between 0.06 and 0.60 g/ml.

2. The oral pharmaceutical composition according to claim 1, in which the packing density is 0.30–0.50 g/ml.

3. The oral pharmaceutical composition according to claim 1, in which each dosage unit contains between 37.5–300 mg of solid Colloidal Bismuth Subcitrate.

4. The oral pharmaceutical composition according to claim 2, in which each dosage unit contains between 37.5–300 mg of solid Colloidal Bismuth Subcitrate.

5. The oral pharmaceutical composition according to claim 1 which contains at least one additional auxiliary medicament.

6. The oral pharmaceutical composition according to claim 1 which contains at least one antimicrobial medicament.

7. The oral pharmaceutical composition according to claim 1 which contains at least one antimicrobial medicament effective against *Helicobacter* (*Campylobacter*) *pylori* selected from the group consisting of the nitro imidazoles, penicillins, cephalosporins, monobactams, penems, tetracyclines, quinolones and macrolides.

8. The oral pharmaceutical composition according to claim 1, in which the dosage units are capsules.

9. The oral pharmaceutical composition according to claim 1, in which the dosage units are capsules selected from the group consisting of gelatin, modified starch and cellulose derivative.

10. A method for treating gastric and intestinal disorders in humans comprising orally administering a composition defined in claim 1 to a human suffering from a gastric or intestinal disorder in an amount effective to relieve the disorder.

11. A method for treating gastric and intestinal disorders in humans comprising orally administering a composition defined in claim 2 to a human suffering from a gastric or intestinal disorder in an amount effective to relieve the disorder.

12. A method for treating gastric and intestinal disorders in humans, comprising orally administering the composition defined in claim 3 to a human suffering from a gastric or intestinal disorder in an amount effective to relieve the disorder.

13. A method for treating gastric and intestinal disorders in humans comprising orally administering the composition defined in claim 4 to a human suffering from a gastric or intestinal disorder in an amount effective to relieve the disorder.

14. A method for treating gastric and intestinal disorders in humans comprising orally administering the composition defined in claim 7 to a human suffering from a gastric or intestinal disorder in an amount effective to relieve the disorder.

15. A method for treating gastric and intestinal disorders in humans comprising orally administering the composition defined in claim 8 to a human suffering from a gastric or intestinal disorder in an amount effective to relieve the disorder.

16. A method for treating gastric and intestinal disorders in humans comprising orally administering the composition defined in claim 1 to a human suffering from a gastric or intestinal disorder.

17. A method for treating gastric and intestinal disorders in humans comprising orally administering the composition defined in claim 2 to a human suffering from a gastric or intestinal disorder.

18. A method for treating gastric and intestinal disorders in humans comprising orally administering the composition defined in claim 3 to a human suffering from a gastric or intestinal disorder.

19. A method for treating gastric and intestinal disorders in humans comprising orally administering the composition defined in claim 4 to a human suffering from a gastric or intestinal disorder.

20. A method for treating gastric and intestinal disorders in humans comprising orally administering the composition defined in claim 7 to a human suffering from a gastric or intestinal disorder.

21. A method for treating gastric and intestinal disorders in humans comprising orally administering the composition defined in claim 8 to a human suffering from a gastric or intestinal disorder.

22. The oral pharmaceutical composition according to claim 1, in which each dosage unit contains between 30 and 600 mg of solid Colloidal Bismuth Subcitrate.

23. The oral pharmaceutical composition according to claim 5, in which the auxiliary medicament is selected from the group consisting of a non-steroidal anti-inflammatory compound, $H_2$-antagonist and synthetic prostaglandin.

24. The oral pharmaceutical composition according to claim 5, in which the auxiliary medicament is an $H_2$-antagonist.

25. The oral pharmaceutical composition according to claim 5, in which the auxiliary medicament is a non-steroidal anti-inflammatory compound.

26. The oral pharmaceutical composition according to claim 5, in which the auxiliary medicament is a synthetic prostaglandin.

27. An oral pharmaceutical composition in unit dosage form comprising a safe and effective amount of solid Colloidal Bismuth Subcitrate (CBS) and, optionally, pharmaceutically acceptable excipients, wherein the packing density of the CBS in each unit of the pharmaceutical composition is sufficiently low to be effective to provide low systemic bismuth absorption and a low transient peak of bismuth blood level after ingestion of said composition.

28. A method for reducing systemic bismuth absorption and the transient peak of bismuth blood level after ingestion of solid Colloidal Bismuth Subcitrate for treatment of gastric and intestinal disorders in humans comprising administering to a human suffering from gastric or intestinal disorder a composition defined in claim 27.

29. A method for reducing systemic bismuth absorption and the transient peak of bismuth blood level after ingestion of solid Colloidal Bismuth Subcitrate for treatment of gastric and intestinal disorders in humans comprising administering to a human suffering from said gastric or intestinal disorder a composition defined in claim 1.

30. A method for the preparation of a solid pharmaceutical composition in unit dosage form comprising:

mixing solid Colloidal Bismuth Subcitrate (CBS) in a amount of between 30 and 600 mg per dosage unit and one or more pharmaceutically acceptable solid excipients;

optionally granulating the resulting mixture and mixing the granulate with one or more additional pharmaceutically acceptable excipients and compressing the mixture so obtained into units, wherein the weight of CBS in grams divided by the volume occupied by the compressed mixture in ml is between 0.06 and 6.0 g/ml.

31. The method according to claim 30, in which the weight of CBS in grams divided by the volume occupied by the compressed mixture in ml is between 0.30 and 0.50 g/ml.

* * * * *